United States Patent [19]

Leonard et al.

[11] Patent Number: 4,973,853
[45] Date of Patent: Nov. 27, 1990

[54] REMOTE SUBSURFACE WATER TEMPERATURE MEASURING APPARATUS WITH BRILLOUIN SCATTERING

[75] Inventors: Donald A. Leonard, Cupertino; Harold E. Sweeney, Menlo Park, both of Calif.

[73] Assignee: GTE Government Systems Corporation, Stamford, Conn.

[21] Appl. No.: 386,383

[22] Filed: Jul. 28, 1989

[51] Int. Cl.$^5$ .................... G01N 15/06; G01J 5/00; G01B 9/02
[52] U.S. Cl. .................. 250/574; 250/231.1; 374/121; 374/127; 374/137; 356/349; 356/43
[58] Field of Search .............. 250/574, 231 R; 374/120, 121, 127, 136, 137, 124, 117; 356/349, 43, 301, 342, 318

[56] References Cited

U.S. PATENT DOCUMENTS

| | | | |
|---|---|---|---|
| 4,057,349 | 11/1977 | Barrett | 356/301 |
| 4,123,160 | 10/1978 | Caputo et al. | 356/43 |
| 4,411,525 | 10/1983 | Ogawa | 356/339 |
| 4,637,716 | 1/1987 | Auweter et al. | 356/349 |
| 4,767,219 | 8/1988 | Bibby | 356/301 |
| 4,823,166 | 4/1989 | Hartog et al. | 356/44 |
| 4,859,065 | 8/1989 | Bibby | 356/44 |
| 4,867,558 | 9/1989 | Leonard et al. | 356/43 |
| 4,867,564 | 9/1989 | Sweeney et al. | 356/349 |

OTHER PUBLICATIONS

Hirschberg et al., "Speed of Sound and Temperature in the Ocean by Brillouin Scattering", *Applied Optics*, vol. 23, No. 15, 8/84, pp. 2624-2628.

Primary Examiner—David C. Nelms
Assistant Examiner—Michael Messinger
Attorney, Agent, or Firm—Douglas M. Gilbert; John F. Lawler

[57] ABSTRACT

Apparatus for measuring the unknown subsurface temperature $T_s$ of a bulk transparent medium such as ocean water comprises a pulsed laser having a high intensity (power per unit area) output beam split into two sub-beams, one of which is a probe beam directed into the ocean water. The intensity of the output beam pulses exceeds a predetermined threshold sufficient to cause stimulated Brillouin scattering within the medium and to produce therefrom a phase-conjugate beam which propagates along the path of the first sub-beam but in the opposite direction. The second sub-beam is reflected by a mirror to and combines with the PC beam and the combined beams are mixed at the cathode of a photodetector which produces a heterodyne frequency that is proportional to the temperature $T_s$. A frequency measuring instrument converts the heterodyne frequency into a temperature value equal to $T_s$.

8 Claims, 2 Drawing Sheets

5°C

10°C

15°C

20°C

25°C

30°C

REMOTE SUBSURFACE WATER TEMPERATURE MEASURING APPARATUS WITH BRILLOUIN SCATTERING

This invention was made with Government support under Contract No. N00014-87-C-0739 awarded by the Department of the Navy. The Government has certain rights in this invention.

RELATED APPLICATIONS

The invention described herein relates generally to the following patent applications:
"APPARATUS FOR AND METHOD OF REMOTELY SENSING SUB-SURFACE WATER WATER TEMPERATURES," Ser. No. 064,371, filed June 27, 1987 now U.S. Pat. No. 4,867,564.
"METHOD OF REMOTELY DETECTING SUBMARINES USING A LASER," Ser. No. 064,375, filed June 22, 1987 now U.S. Pat. No. 4,867,558.
"REMOTE SUBSURFACE WATER TEMPERATURE MEASURING APPARATUS," Ser. No. 387,735, filed Aug. 1, 1989.

BACKGROUND OF THE INVENTION

This invention relates to the remote measurement of the properties of transparent media such as subsurface ocean temperatures profiles and in particular to improved apparatus for measuring such temperature profiles from surface or subsurface vessels or aircraft.

There are several applications for remotely sensing or measuring the temperature of a bulk transparent medium such as water. One of such applications is the sounding of temperature profiles in the ocean which is useful for a variety of oceanographic purposes such as measuring the depth of the thermocline, sensing internal waves, measuring heat content of oceans for meteorological applications and mapping acoustical propagation paths sensitive to temperature gradients. Insitu temperature sensors such as thermistors, thermocouples, etc. have been used in the past for these purposes but, because they are not remote sensors, are slow and awkward. A remote sensing technique in wide use is the monitoring of thermal radiation; this technique, however, is limited to measuring predominately surface temperatures.

This invention is directed to improved apparatus for remotely measuring temperature within, i.e., below the surface of suitable transparent media or substances, as for example sea water.

OBJECTS AND SUMMARY OF THE INVENTION

A general object of the invention is the provision of apparatus for measuring the subsurface temperature of a transparent substance remotely and substantially instantly.

A further object is the provision of such apparatus that is relatively compact and highly portable.

Another object is the provision of a measurement technique that has a high signal-to-noise ratio and therefore produces highly accurate measurements.

A further object is the provision of such apparatus in which the irradiance of the received return signal from the target substance is relatively high.

These and other objects of the invention are achieved with apparatus consisting of a pulsed laser having a highly intense output beam capable of producing stimulated Brillouin scattering (SBS) in the medium under test. A beam splitter splits this pulsed beam into two sub-beams and directs one sub-beam designated the probe beam, into the transparent medium of unknown temperature to produce a phase-conjugate beam from the medium. The return phase-conjugate sub-beam and the other sub-beam are optically mixed in a photodetector to derive a difference frequency proportional to the unknown temperature of the medium. And, a frequency converter translates the difference frequency to a value corresponding to the unknown temperature.

BRIEF DESCRIPTION OF THE DRAWINGS

For a better understanding of the invention as well as other objects and further features thereof, reference is made to the following description which is to be read in conjunction with the accompanying drawings wherein.

DESCRIPTION OF PREFERRED EMBODIMENT

Figure 1:
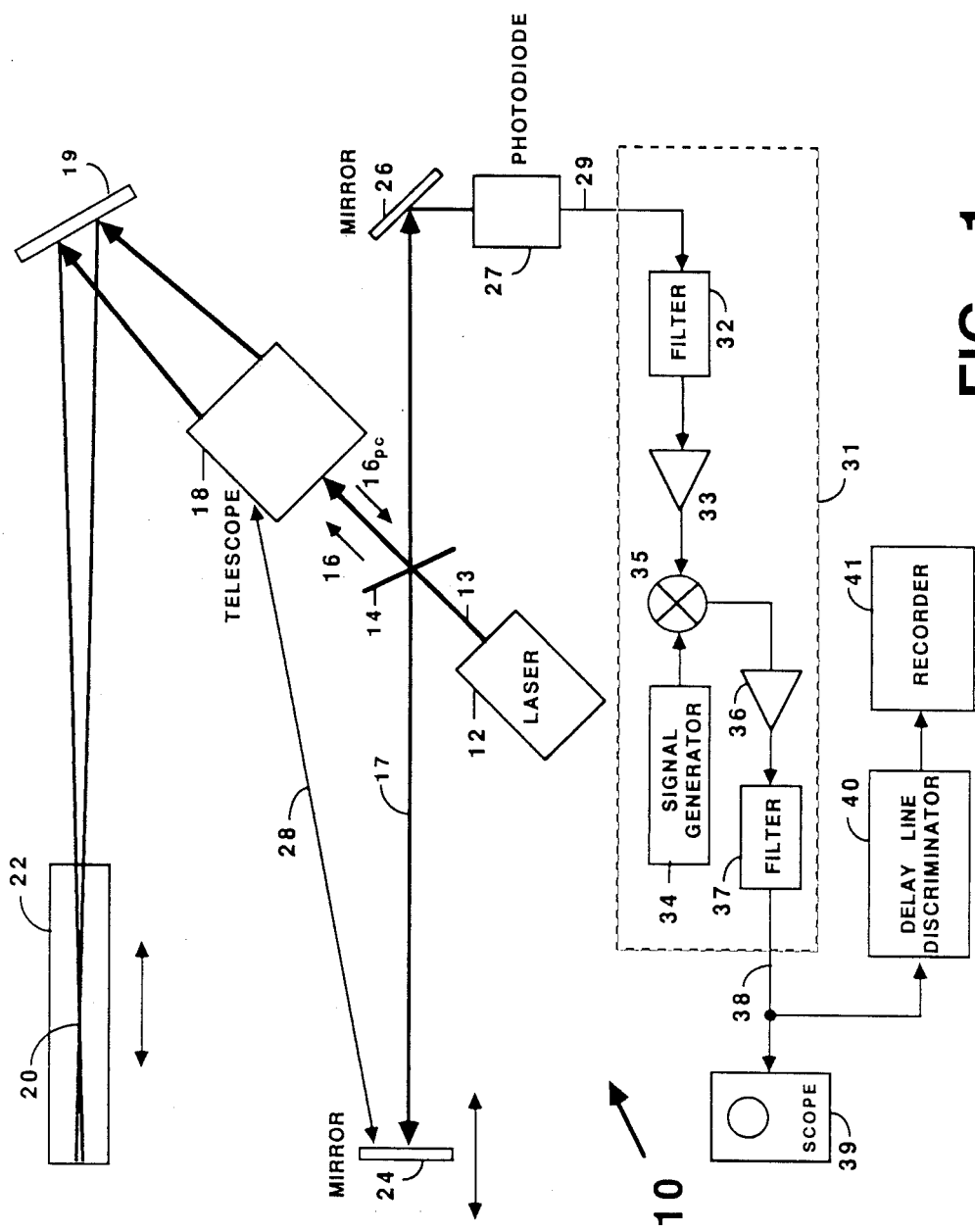
FIG. 1 is a schematic drawing of apparatus for optically measuring temperature in accordance with the invention.
Figure 2A:
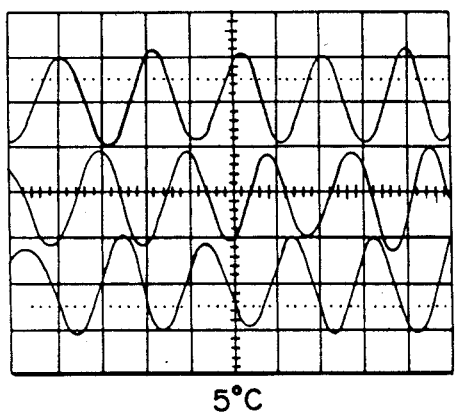
FIGS. 2A through 2F are representations of several actual heterodyne waveforms as a function of water temperature at 5° C. intervals as derived from the apparatus depicted in FIG. 1.
Figure 2B:
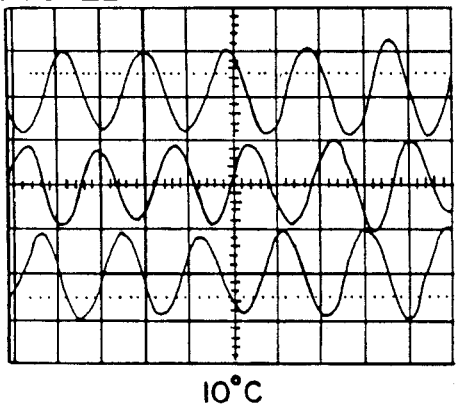
Figure 2C:
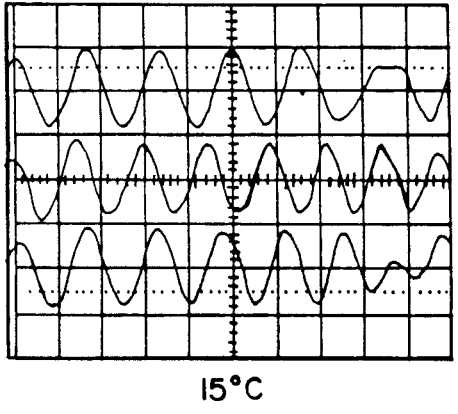
Figure 2D:
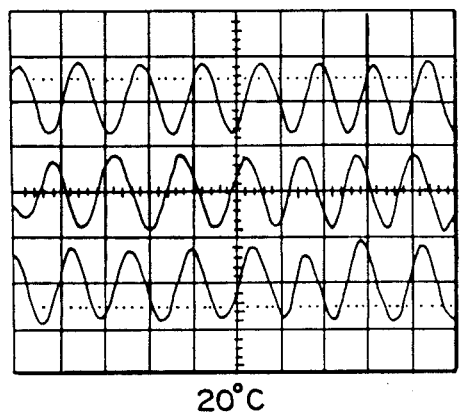
Figure 2E:
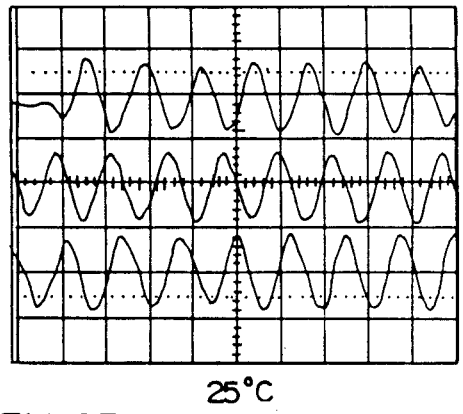
Figure 2F:
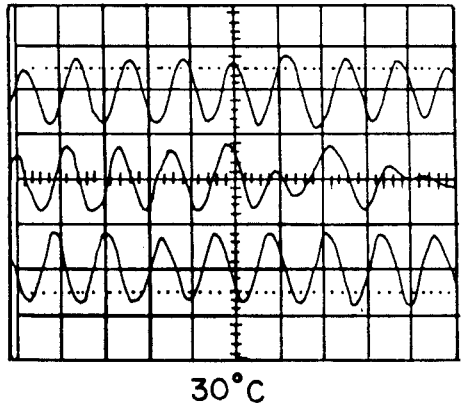

Referring now to the drawings, FIG. 1 illustrates temperature measuring apparatus 10 in which a pulsed laser 12 generates an intense output beam 13. Beam 13 is incident on and split by a beam splitter 14 into a first sub-beam 16 which passes through splitter 14 and a second sub-beam 17 which is reflected thereby. Sub-beam 16 passes through a lens or telescope 18 to a mirror 19 and is focussed thereby to a focal point 20 in a transparent medium 22 such as water. Telescope 18 is adjustable so as to enable adjustment of the location of focal point 20 to various selected locations or depths within medium 22 as suggested by the proximate double-headed arrow. The unknown temperature of interest, designated $T_S$, is the temperature of medium 22 at focal point 20.

Sub-beam 17 propagates from splitter 14 to and is reflected by a mirror 24 along the same path back to splitter 14. The spacing of mirror 24 from splitter 14 is variable as indicated by the adjacent double-headed arrow.

The intensity of the pulsed output beam 13, i.e., the intensity or irradiance of the pulses from laser 12 exceeds a predetermined threshold level at which sub-beam 16 produces stimulated Brillouin scattering in cell 22 resulting in the generation of a phase-conjugate or "time-reversed" beam whose ray runs along the same trajectory as but in opposite direction to sub-beam 16. The direction of the PC beam is designated by the arrow $16_{pc}$. This phenomenon, called optical phase conjugation, is well known and is described in detail in articles entitled *Optical Phase Conjugation* by V. V. Shkunov et al, Scientific American, pages 54–59 (September 1985) and *Applications of Optical Phase Conjugation* by D. M. Pepper, Scientific American, pages 74–83 (January 1986).

The Brillouin backscatter optical wave from a spontaneously generated phonon interacts with the probe beam and the interaction produces a traveling electric field that travels exactly at the sound velocity in the particular substance. If the light intensity is great enough and the electrostrictive coefficient of the medium is sufficiently strong, this traveling electric field will create an acoustic field which aligns itself in a column with the probe beam and the backscattered beam at the expense of scattering in other directions. Hence the collection of light is more efficient in the SBS case.

The presence of the induced electric field traveling at the sound velocity can be derived in the following way. Assume that an electromagnetic wave (the probe laser) propagates in a substance in the $+x$ direction with velocity c, then the electric field may be written as $$E_1 = E_0 \sin(\omega_1 t - \omega_1 x/c) \quad (1)$$

where,
$E_0$ = magnitude of the wave,
$\omega$ = frequency, and
$t$ = time parameter,
and assume that a wave of different frequency (the Brillouin scattering) propagates in the $-x$ direction, the electric field of which is written as, $$E_2 = E_0 \sin(\omega_2 t + \omega_2 x/c), \quad (2)$$

where, $\omega_2$ = frequency of the second wave.
The total electric field in their common region is $$E = E_1 + E_2 = E_0[\sin(\omega_1 t - \omega_1 x/c) + \sin(\omega_2 t + \omega_2 x/c)] \quad (3)$$

which can be arranged by trigonometric identities to the form $$E = 2E_0\{\sin\tfrac{1}{2}[(\omega_1+\omega_2)t - (\omega_1-\omega_2)x/c]\}\{\cos\tfrac{1}{2}[(\omega_1-\omega_2)t - (\omega_1+\omega_2)x/c]\} \quad (4)$$

which is of the form of a high frequency $(\omega_1 + \omega_2)$ signal modulated with a low frequency $(\omega_1 - \omega_2)$ envelope. The velocity of the envelope is found by making its argument constant, i.e., $$(\omega_1 - \omega_2)t - (\omega_1 + \omega_2)x/c = K. \quad (5)$$

The envelope velocity is therefore $$dx/dt = (\omega_1 - \omega_2)c/(\omega_1 + \omega_2) \quad (6)$$
$$= (f_1 - f_2)c/(f_1 + f_2).$$

In the case of Brillouin scattering $f_2$ has been produced by Doppler shift by interacting with an acoustic wave at velocity v. The Doppler equation, namely $$f_2 = f_1(c-v)/(c+v), \quad (7)$$

which when solved results in the following expression:

$$c = (f_1 + f_2)v/(f_1 - f_2) \quad (8)$$

A substitution into the prior expression (6) for dx/dt yields dx/dt = v. The envelope of the composite electric field wave therefore travels exactly at the acoustic velocity.

In order to achieve SBS, a predetermined threshold intensity level for the optical probe beam must be exceeded. This intensity level must be sufficient so that the following relationship exists:

$$\exp[GIL] \gtrsim 10^{13}$$

or, $$\exp[GIL] \gtrsim \exp[30],$$

(since $10^{13} = \exp[30]$).

Or more simply, the intensity, $I \gtrsim 30/GL$, where,
G = a gain parameter which is a property of the medium, m/W
I = intensity of the optical probe beam (W/m$^2$) and,
L = interaction length, m,
see *Principles of Phase Conjugation* by Zel'dovich et al., Springer-Verlag, Vol. 42, page 29, Springer Series on Optical Sciences (Springer Verlag Berlin Heidelberg, 1985). (For water G is typically $5 \times 10^{-11}$ m/W.)

The sound velocity in water is related to the temperature and salinity and is given in the article entitled *Development of Simple Equations for Accurate and More realistic Calculation of the Speed of Sound in Sea Water* by C. C. Leroy, Journal of Acoustical Society of America, No. 216, page 216 (1969):

$$v = 1492.9 + 3(T-10) - 0.006(T-10)^2 - 0.04(T-18)^2 + 1.2(S-35) - 0.01(T-18)(S-35) + Z/61 \quad (9)$$

where,
T = temperature in degrees C.,
S = salinity in parts per thousand,
Z = depth in meters.

The phase conjugate of sub-beam 16, designated $16_{pc}$, propagates from medium 22 precisely along the path of sub-beam 16 except in the opposite direction to mirror 19 and is reflected thereby through lens 18 to splitter 14 from which it is reflected to mirror 26 and ultimately to photodetector 27, such as a photodiode. Sub-beam 17 reflected from mirror 24 passes through splitter 14 to mirror 26 and is reflected thereby to photodetector 27. It is important that the pulses comprising sub-beam 17 and the pulses comprising PC beam $16_{pc}$ arrive at the active mixing surface of photodetector 27 at the same time for effective heterodyning of these two signals. Since there is no optical storage mechanism, if the pulses from the two beams are not properly timed to arrive at the photodetector at substantially the same instant, the two pulses will not mix with each other. To this end, the optical spacing of both focal point 20 and mirror 24 from photodetector 27 are the same. The adjustable spacing between mirror 24 and splitter 14 accommodates this requirement. The adjustment of the location of focal point 20 in medium 22 may also be directly related to adjustment of the position of mirror 24 by means of a mechanical, electromechanical or other suitable link or connection between lens 18 and mirror 24 as indicated by line 28 between these components.

A phase-conjugated beam derived from SBS has its optical frequency shifted by a frequency that produces an acoustical wavelength in the water equal to half the optical wavelength, i.e.

$$\Delta\nu = (2)\frac{v_a n}{\lambda} \quad (10)$$

where,
$\Delta\nu$ = the optical frequency shift,
$v_a$ = the acoustic velocity in water, n = the index of refraction in water, and
λ = the wavelength of the incident beam in a vacuum.

Photodetector 27 mixes sub-beam 17 and beam $16_{pc}$ and produces at its output 29 a difference frequency, δf, that is proportional to the temperature $T_s$. This frequency may be as high as 8 GHz. In order to enable conversion of a δf of this magnitude to an analog temperature value with conventional oscilloscope/recorder equipment, it is desirable to further mix photodetector output 29 to down convert the latter to a lower more manageable frequency. This is accomplished with down converter equipment enclosed within broken lines 31 and comprising a filter 32, an amplifier 33, a signal generator 34, a mixer 35, an amplifier 36 and a filter 37. High-pass filter 32 rejects the basic pulse components in output 29 but preserves the SHF (super high frequency) signal. Amplifier 33 increases the signal level into double-balanced mixer 35 driven by signal generator 34. In fresh water the SHF signal is typically 7.1 to 7.5 GHz; setting the signal generator to 6550 MHz produces an IF (intermediate frequency) between 550 and 950 MHz for convenient viewing on a real time oscilloscope (39) such as Tektronix Model No. 7104. The output 38 of filter 37 is observed by scope 39, and is converted to a voltage by a wide band delay line discriminator 40 which feeds a chart recorder 41. Delay line discriminator 40 is designed to operate between 500 to 1000 MHz.

FIG. 2 shows a series of photographs of the display screen from oscilloscope 39 depicting the heterodyne waveform as a function of medium (water) temperature from 5° to 30° C. at 5 degree intervals. The change in frequency is clearly seen in these photographs at a high signal-to-noise ratio.

While the invention has been described with reference to its preferred embodiment, it will be understood by those skilled in the art that various changes may be made and equivalents may be substituted for the elements thereof without departing from the true spirit and scope of the invention. In addition, many modifications may be made to adapt a particular situation or material to the teaching of the invention without departing from its essential teaching.

What is claimed is:

1. Apparatus for remotely measuring the unknown temperature $T_s$ of a transparent medium, comprising:
   a pulsed laser having an output beam, said output beam comprising a plurality of pulses each having an irradiance such that
   $I \geq 30/GL$ where,
   G is a gain parameter of said transparent medium (m/W),
   I is the intensity of said output beam pulse, (W/m²), and
   L is the interaction length (m);
   means for directing said output beam into said medium whereby to produce stimulated Brillouin scattering and to generate a phase-conjugate beam emanating from said medium;
   a photodetector spaced so as to receive said phase-conjugate beam and said laser output beam at substantially the same time to produce a nonoptical difference frequency proportional to the temperature $T_s$; and
   means for converting said difference frequency into a temperature value.

2. Apparatus according to claim 1 in which said first-named beam directing means comprises an adjustable lens for directing said beam into said medium whereby to vary the depth of the beam focussing point in said medium.

3. Apparatus for remotely measuring the temperature $T_s$ of a transparent medium, comprising:
   a pulsed laser having an output beam with an intensity sufficient to cause stimulated Brillouin scattering when said output beam is directed into said medium and thereby to generate a phase-conjugate beam emanating from said medium;
   a photodetector;
   means for simultaneously directing said phase-conjugate beam and a portion of said laser output beam onto said photodetector to produce a difference frequency proportional to the temperature $T_s$; and
   means for converting said difference frequency into the temperature value of $T_s$.

4. Apparatus according to claim 3 with means for adjustably focussing said output beam to a plurality of selected points at different locations within said medium whereby to measure the medium temperatures at said points, and means for adjusting the range of said portion of said laser output beam from said photodetector to be equal to the range of each of said selected points from said photodetector.

5. Apparatus according to claim 4 in which said medium consists of a body of water.

6. Apparatus for remotely measuring the subsurface temperatures $T_s$ of sea water comprising:
   laser means for generating a pulsed laser beam having a plurality of pulses of wavelength $\lambda_1$, said laser means including means for directing said pulsed laser beam into the sea water, said pulsed laser beam having an intensity sufficient to cause stimulated Brillouin scattering in the sea water and thereby generating a return plurality of phase-conjugate beam pulses of wavelength $\lambda_2$ emanating from the sea water;
   a photodetector sensitive to an optical spectrum including the wavelengths $\lambda_1$ and $\lambda_2$;
   means for simultaneously directing said phase-conjugate beam and at least a portion of said pulsed laser beam onto said photodetector such that pulses from both of said beams have a time coincidence at said photodetector;
   means for extracting a difference frequency δf from said photodetector; and
   means for converting said δf into a value corresponding to the temperature $T_s$.

7. Apparatus according to claim 6 in which said wavelength $\lambda_1$ is in the blue-green spectrum.

8. Apparatus as in claim 6 further comprising:
   airborne platform means for housing each of said aforementioned means, said platform means including an optical window for transmitting said pulsed beam and for receiving said return phase-conjugate beam.

* * * * *